United States Patent
Martin

(10) Patent No.: US 12,178,640 B2
(45) Date of Patent: Dec. 31, 2024

(54) VISUALIZATION OF REFLECTORS IN INTRALUMINAL ULTRASOUND IMAGES AND ASSOCIATED SYSTEMS, METHODS, AND DEVICES

(71) Applicant: PHILIPS IMAGE GUIDED THERAPY CORPORATION, San Diego, CA (US)

(72) Inventor: Karl Heath Martin, Rancho Cordova, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 0 days.

(21) Appl. No.: 17/065,420

(22) Filed: Oct. 7, 2020

(65) Prior Publication Data

US 2021/0100527 A1    Apr. 8, 2021

Related U.S. Application Data

(60) Provisional application No. 62/912,327, filed on Oct. 8, 2019.

(51) Int. Cl.
*A61B 8/00* (2006.01)
*A61B 8/08* (2006.01)
*A61B 8/12* (2006.01)

(52) U.S. Cl.
CPC ............ *A61B 8/085* (2013.01); *A61B 8/0841* (2013.01); *A61B 8/12* (2013.01); *A61B 8/445* (2013.01); *A61B 8/463* (2013.01)

(58) Field of Classification Search
CPC ......... A61B 8/085; A61B 8/0841; A61B 8/12; A61B 8/445; A61B 8/463
See application file for complete search history.

(56) References Cited

U.S. PATENT DOCUMENTS

| | | |
|---|---|---|
| 6,200,268 B1 | 3/2001 | Vince |
| 6,381,350 B1 | 4/2002 | Klingensmith |
| 7,074,188 B2 | 7/2006 | Nair |

(Continued)

OTHER PUBLICATIONS

Duck, Francis A., "Nonlinear Acoustics in Diagnostic Ultrasound", Ultrasound in Medicine & Biology, vol. 28, No. 1, 2002, pp. 1-18.

(Continued)

*Primary Examiner* — Amal Aly Farag

(57) ABSTRACT

Systems, methods, and devices for visualizing a reflector in a lumen of a patient are provided. In one embodiment, a system for visualizing a reflector includes an intraluminal ultrasound imaging catheter in communication with a processor circuit. The processor circuit is configured to receive, from the intraluminal ultrasound imaging catheter, ultrasound image signals representative of the lumen and the reflector, generate first ultrasound image data based on the ultrasound image signals, generate second ultrasound image data based on a portion of the ultrasound image signals associated with a second frequency different from the transmit frequency, and output a visualization based on the first and second ultrasound image data to a display. In some aspects, the visualization may serve to identify and distinguish nonlinear reflectors from linear reflectors in the combined image.

15 Claims, 7 Drawing Sheets

(56) References Cited

U.S. PATENT DOCUMENTS

| | | | |
|---|---|---|---|
| 7,175,597 B2 | 2/2007 | Vince | |
| 7,215,802 B2 | 5/2007 | Klingensmith | |
| 7,359,554 B2 | 4/2008 | Klingensmith | |
| 7,463,759 B2 | 12/2008 | Klingensmith | |
| 7,846,101 B2 | 12/2010 | Eberle | |
| 9,265,481 B2 | 2/2016 | Hancock | |
| 10,269,096 B2 | 4/2019 | Hancock | |
| 2001/0029336 A1* | 10/2001 | Teo | A61B 8/06 600/442 |
| 2006/0270934 A1* | 11/2006 | Savord | G01S 15/8993 600/437 |
| 2008/0051660 A1* | 2/2008 | Kakadaris | A61B 8/488 600/454 |
| 2008/0200815 A1 | 8/2008 | Van Der Steen | |
| 2010/0246332 A1* | 9/2010 | Huang | A61B 8/12 367/181 |
| 2010/0298709 A1 | 11/2010 | Needles | |
| 2011/0160586 A1* | 6/2011 | Li | G01S 15/8952 600/443 |
| 2012/0283569 A1* | 11/2012 | Ciompi | A61B 8/4461 600/463 |
| 2014/0100440 A1 | 4/2014 | Cheline | |
| 2014/0180087 A1* | 6/2014 | Millett | A61B 5/02158 600/437 |
| 2014/0236017 A1* | 8/2014 | Degertekin | A61B 8/12 600/462 |
| 2014/0270429 A1* | 9/2014 | Nair | G06K 9/6293 382/128 |
| 2014/0350404 A1* | 11/2014 | Rajguru | A61B 8/466 600/443 |
| 2015/0272601 A1* | 10/2015 | Dixon | A61N 7/00 604/24 |
| 2016/0007947 A1* | 1/2016 | Spencer | A61B 8/0841 600/424 |
| 2019/0069883 A1 | 3/2019 | He | |

OTHER PUBLICATIONS

Averkiou, Michalakis A. "Tissue Harmonic Imaging", IEEE Ultrasonics Symposium, 2000, pp. 1563-1572.

Hope Simpson, David et al "Pulse Inversion Doppler: A New Method for Detecting Nonlinear Echoes from Microbubble Contrast Agents", IEEE Transactions on Ultrasonics, Ferroelectrics, and Frequency Control, vol. 46, No. 2, Mar. 1999, pp. 372-382.

Wang, Zhuochen et al "An Array Transmitter for Dual-Frequency Contrast Enhanced Intravasular Ultrasound Imaging", 2014 IEEE International Unltrasonics Symposium Proceedings, pp. 2104-2107.

Diamantis, Konstantinos et al "Development of Super-Resolution Sharpenss-Based Axial Localization for Ultrasound Imaging", IEEE Access, vol. 7, 2019. pp. 6297-6309.

Brown, J. et al "Investigation of Microbubble Detection Methods for Super-Resolution Imaging of Microvasculature", 2017 IEEE.

* cited by examiner

VISUALIZATION OF REFLECTORS IN INTRALUMINAL ULTRASOUND IMAGES AND ASSOCIATED SYSTEMS, METHODS, AND DEVICES

CROSS-REFERENCE TO PRIOR APPLICATION

This application claims the benefit of U.S. Provisional Patent Application Ser. No. 62/912,327, filed Oct. 8, 2019 which is hereby incorporated by reference herein.

TECHNICAL FIELD

The subject matter described herein relates to a system for medical imaging. In particular, the present disclosure describes aspects related to acquisition and display intraluminal ultrasound images associated with nonlinear and linear ultrasound frequencies.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

IVUS imaging may be used to identify and locate blood vessel features such as the vessel wall, adventitia, flowing blood, stenoses, calcium deposits, and/or medical implants, such as stents. However, in some aspects, conventional B-mode IVUS images may not adequately depict some features, including stents and calcium deposits, such that they can be easily distinguished or identified from other features, such as a vessel wall. Accordingly, identifying and locating different anatomical and medical features in conventional IVUS images can be challenging.

SUMMARY

Disclosed are systems, methods, and devices for identifying a visualizing in a lumen of a patient. For example, a system for visualizing a reflector may include an intraluminal imaging device in communication with a processor circuit. The processor circuit is configured to receive ultrasound image data from the imaging device, where the image data is representative of both linear and nonlinear reflections. For example, the imaging device may be used in a blood vessel of a patient that includes calcium deposits and/or a stent. Calcium deposits and stents may be considered nonlinear reflectors, as they tend to reflect ultrasound energy in a nonlinear fashion. In nonlinear reflections, the frequencies of the echoes reflected by an object are different from the frequencies emitted by the ultrasound transducer. When imaged with sufficient acoustic intensity, nonlinear reflectors such as calcium deposits and stents generate nonlinear reflections that include harmonic frequencies of the frequencies transmitted by the ultrasound transducer. The processor circuit generates a linear ultrasound image, such as a B-mode image corresponding to linear portions of the image data, and a nonlinear image corresponding to nonlinear portions of the image data. The processor circuit then outputs a combined image to a display that includes the linear ultrasound image and a graphical representation of the nonlinear image. In some aspects, the graphical representation may serve to identify and distinguish nonlinear reflectors from linear reflectors in the combined image. Accordingly, workflows can be improved and the confidence of diagnostic procedures that involve identifying and/or locating nonlinear reflectors can be increased.

According to one embodiment of the present disclosure, an apparatus for visualizing a reflector in a lumen of a patient includes: a processor circuit communicatively coupled to an intraluminal ultrasound imaging catheter, wherein the processor circuit is configured to: receive, from the intraluminal ultrasound imaging catheter, ultrasound image signals representative of the lumen and the reflector, wherein the ultrasound image signals are associated with a transmit frequency of the intraluminal ultrasound imaging catheter; generate, in a first processing path, first ultrasound image data based on the ultrasound image signals; identify, in a second processing path, a portion of the ultrasound image signals associated with a second frequency different from the transmit frequency; generate, in the second processing path, second ultrasound image data based on the portion of the ultrasound image signals; and output, to a display in communication with the processor circuit, one or more ultrasound images based on the first ultrasound image data and the second ultrasound image data.

In some embodiments, the processor circuit is configured to: apply a first bandpass filter to the ultrasound image signals to generate the first ultrasound image data; and apply a second bandpass filter to the ultrasound image signals to identify the portion of the of the ultrasound image signals associated with the second frequency. In some aspects, the first bandpass filter is associated with a first frequency band that includes the transmit frequency, and wherein the second bandpass filter is associated with a second frequency band that includes a harmonic of the transmit frequency and is non-overlapping with the first frequency band. In some embodiments, the second frequency band is higher than the first frequency band. In some embodiments, the one or more ultrasound images comprises: a first ultrasound image based on the first ultrasound image data; and a second ultrasound image based on the second ultrasound image data. In some embodiments, the processor is configured to output, to the display, a numerical representation associated with the second ultrasound image.

In some embodiments, the processor circuit is configured to compute a geometrical value of the reflector based on the second ultrasound image data, and wherein the numerical representation represents the geometrical value. In some embodiments, wherein the processor circuit is configured to generate a composite image based on the first ultrasound image data and the second ultrasound image data. In some embodiments, the processor circuit is configured to: generate a first ultrasound image based on the first ultrasound image data; and generate a second ultrasound image based on the second ultrasound image data. In some embodiments, the processor circuit is configured to generate the composite image by overlaying the second ultrasound image on the first ultrasound image, and wherein portions of the composite image corresponding to the second ultrasound image comprise a different color from portions of the composite image corresponding to the first ultrasound image. In some embodiments, the apparatus further includes the intraluminal ultrasound imaging catheter. In some embodiments, the intraluminal ultrasound imaging catheter comprises an intravascular ultrasound (IVUS) imaging catheter.

According to another embodiment of the present disclosure, a method for visualizing a reflector in a lumen of a patient includes: receiving, by a processor circuit, ultrasound image signals obtained by an intraluminal ultrasound imaging catheter, wherein the ultrasound image signals are representative of a lumen and a reflector, and wherein the ultrasound image signals are associated with a transmit frequency of the intraluminal ultrasound imaging catheter; generating, in a first processing path, first ultrasound image data based on the ultrasound image data; identifying, in a second processing path, a portion of the ultrasound image signals associated with a second frequency different from the transmit frequency; generating, in the second processing path, second ultrasound image data based on the portion of the ultrasound image signals; and outputting, to a display in communication with the processor circuit, one or more ultrasound images based on the first ultrasound image data and the second ultrasound image data.

In some embodiments, the method further includes applying a first bandpass filter to the ultrasound image signals to generate the first ultrasound image data; and applying a second bandpass filter to the ultrasound image signals to identify the portion of the ultrasound image signals associated with the second frequency. In some aspects, the first bandpass filter is associated with a first frequency band that includes the transmit frequency, and wherein the second bandpass filter is associated with a second frequency band that includes a harmonic of the transmit frequency and is non-overlapping with the first frequency band. In some embodiments, the second frequency band is higher than the first frequency band. In some embodiments, outputting the one or more ultrasound images to the display comprises: outputting a first ultrasound image based on the first ultrasound image data; and outputting a second ultrasound image based on the second ultrasound image data.

In some embodiments, the method further includes generating a numerical representation associated with the second ultrasound image; and outputting the numerical representation to the display. In some embodiments, generating the numerical representation comprises computing a geometrical value of the reflector. In some embodiments, outputting the one or more ultrasound images to the display comprises generating a composite image based on the first ultrasound image data and the second ultrasound image data. In some embodiments, generating the composite image comprises: generating a first ultrasound image based on the first ultrasound image data; generating a second ultrasound image based on the second ultrasound image data; and overlaying the second ultrasound image on the first ultrasound image. In some embodiments, portions of the composite image corresponding to the second ultrasound image comprise a different color from portions of the composite image corresponding to the first ultrasound image.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
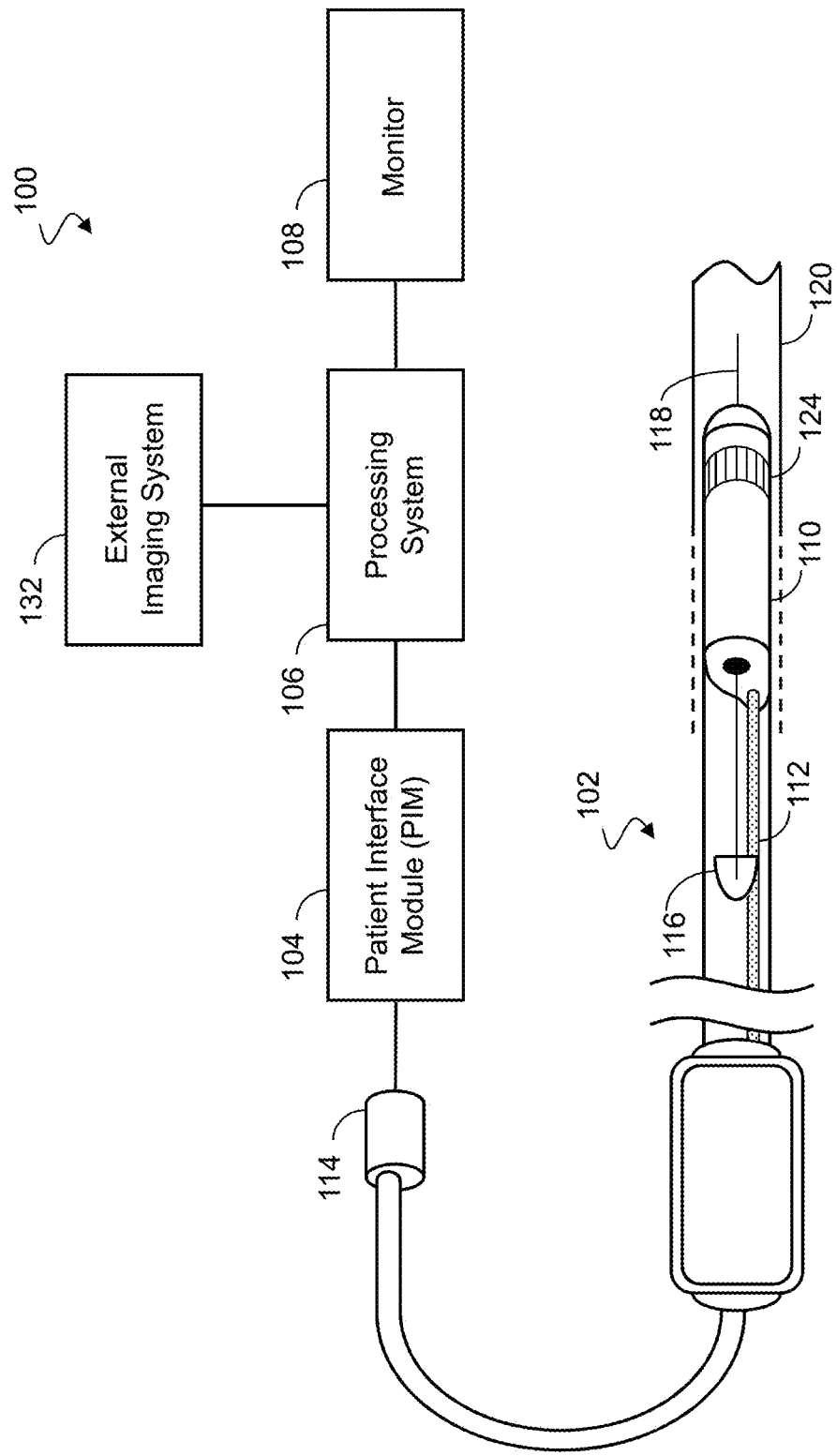
FIG. 1 is a diagrammatic schematic view of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system 100 for visualizing nonlinear reflectors in an ultrasound image, according to aspects of the present disclosure. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized, shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132, in some embodiments.

The intraluminal imaging system 100 (or intravascular imaging system) can be any type of imaging system suitable for use in the lumens or vasculature of a patient. In some embodiments, the intraluminal imaging system 100 is an intravascular ultrasound (IVUS) imaging system. In other embodiments, the intraluminal imaging system 100 may include for example systems configured for forward looking intravascular ultrasound (FL-IVUS) imaging, intravascular photoacoustic (IVPA) imaging, intracardiac echocardiography (ICE), transesophageal echocardiography (TEE), optical coherence tomography (OCT), and/or other suitable imaging modalities.

It is understood that the system 100 and/or device 102 can be configured to obtain any suitable intraluminal imaging data. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with a vessel or lumen 120 of a patient. The device 102 may be sized and shaped (and/or configured) for insertion into the vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator may be positioned away from the patient and/or out of the sterile medical environment.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, an intraluminal ultrasound imaging device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. For example, a rotational ultrasound imaging catheter may comprise a drive cable positioned within an elongate flexible sheath, and a transducer element positioned at a distal portion of the drive cable and configured to rotate with the drive cable. In a rotational ultrasound imaging system, the PIM 104 may comprise a rotational interface for providing rotation to the drive cable while maintaining an electrical connection with the ultrasound transducer at the distal portion of the drive cable.

The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can include a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 100,000 acoustic elements, including values such as 2 acoustic elements, 4 acoustic elements, 36 acoustic elements, 64 acoustic elements, 128 acoustic elements, 500 acoustic elements, 812 acoustic elements, 1,000 acoustic elements, 10,000 acoustic elements, 65,000 acoustic elements, and/or other values both larger and smaller.

The PIM 104 transfers the received echo signals to the processing system 106 where the ultrasound image (including the flow information) is reconstructed and displayed on the monitor 108. In some aspects, the monitor 108 may be referred to as a display or a visualization device. In some aspects, the monitor or display 108 is configured to show a visualization or interface that includes one or more images and/or graphical representations. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110. In some embodiments, the PIM 104 includes a mechanical interface configured to control the intraluminal device 102 to perform a pullback operation. For example, the mechanical interface may comprise a pullback device coupled to a proximal end of the intraluminal imaging device 102 and configured to provide for rotational movement of the intraluminal device 102 and/or longitudinal movement of the intraluminal device 102. The PIM 104 may facilitate a pullback procedure by activating a rotational component (e.g., a motor) of the pullback device and/or a longitudinal component of the pullback device for advancing or retracting the intraluminal device 102 within the vessel 120. In phased array IVUS, for example, the pullback device may provide for longitudinal, but not rotational movement of the IVUS catheter. In some embodiments, the pullback device comprises a different component separate from the PIM 104. In some embodiments, the PIM 104 and the pullback device are positioned within a same housing.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the vessel or heart, blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Philips and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, eight, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. This workflow may include performing a pre-stent plan to determine the state of a lumen and potential for a stent, as well as a post-stent inspection to determine the status of a stent that has been positioned in a lumen. The workflow may be presented to a user in a display screen.

The external imaging system 132 can be configured to obtain x-ray, radiographic, angiographic (e.g., with contrast), and/or fluoroscopic (e.g., without contrast) images of the body of a patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MM) to obtain images of the body of the patient (including the vessel 120). The processing system 106 can utilize the images of the body of the patient in conjunction with the intraluminal images obtained by the intraluminal device 102.

Figure 2:
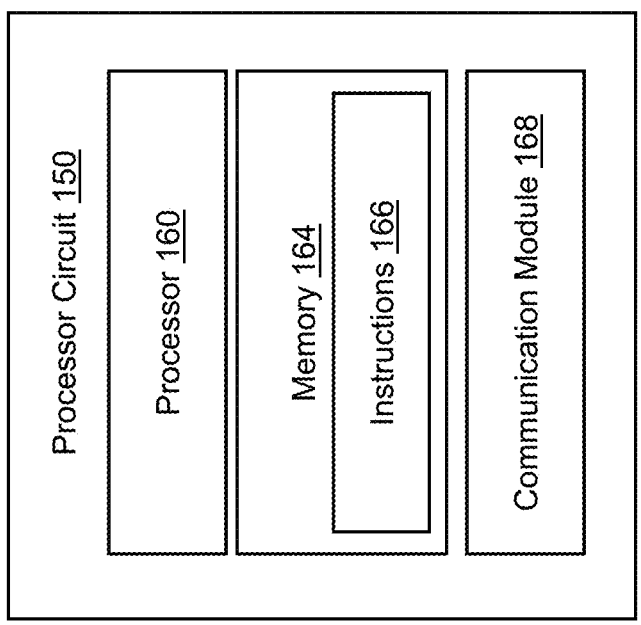
FIG. 2 is a schematic diagram of a processor circuit, according to aspects of the present disclosure.

FIG. 2 is a schematic diagram of a processor circuit 150, according to aspects of the present disclosure. The processor circuit 150 may be implemented in the ultrasound imaging system 100, or other devices or workstations (e.g., third-party workstations, network routers, etc.) as necessary to implement one or more methods as disclosed herein, including the methods 500a and 500b shown in FIGS. 7a and 7b, respectively. As shown, the processor circuit 150 may include a processor 160, a memory 164, and a communication module 168. These elements may be in direct or indirect communication with each other, for example via one or more buses.

The processor 160 may include a central processing unit (CPU), a graphical processing unit (GPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 160 may also comprise another hardware device, a firmware device, or any combination thereof configured to perform the operations described herein. The processor 160 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 160, cause the processor 160 to perform the operations described herein, including one or more steps of the methods 500a and/or 500b illustrated in FIGS. 7a and 7b, respectively. Instructions 166 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 168 can include any electronic circuitry and/or logic circuitry to facilitate direct or indirect communication of data between the processor circuit 150, and other processors or devices. In that regard, the communication module 168 can be an input/output (I/O) device. In some instances, the communication module 168 facilitates direct or indirect communication between various elements of the processor circuit 150 and/or the ultrasound imaging system 100. The communication module 168 may communicate within the processor circuit 150 through numerous methods or protocols. Serial communication protocols may include but are not limited to US SPI, $I^2C$, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media such as a USB flash drive or memory stick.

Figure 3:
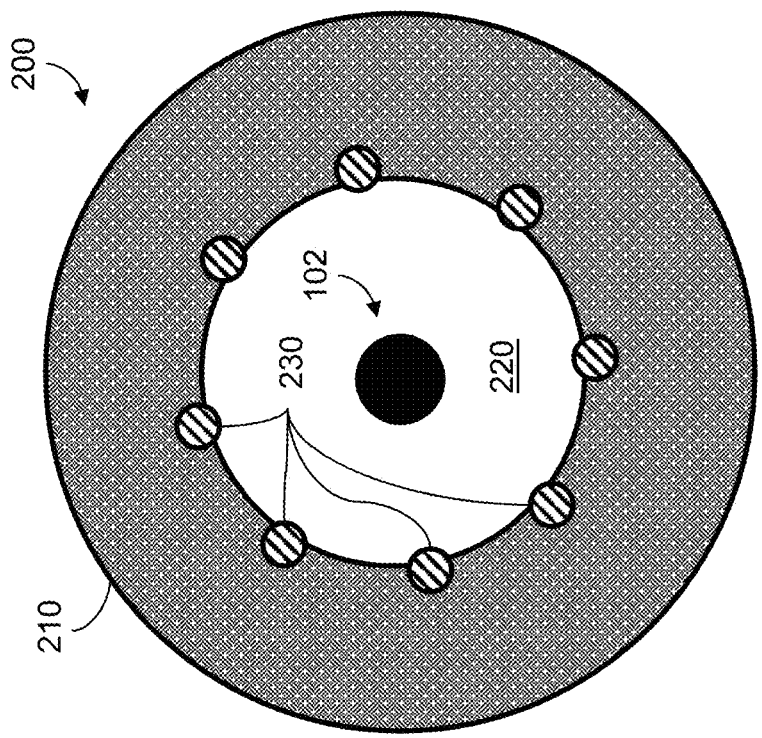
FIG. 3 is a diagrammatic cross-sectional view of a blood vessel including a stent, according to aspects of the present disclosure.

FIG. 3 is a diagrammatic cross-sectional view of a blood vessel 200 that includes a stent having a plurality of stent struts 230 positioned adjacent a wall 210 of the vessel 200. The wall 210 of the vessel 200 may comprise the tissue structure that defines the lumen 220 of the vessel 200. An intraluminal imaging device 102, which may include an IVUS imaging catheter, is positioned within the lumen 220. In some aspects, the intraluminal imaging device 102 may be configured to insonate the vessel 200 at a frequency selected or optimized to obtain images of the wall 210. For example, the intraluminal imaging device may be configured to emit a range or band of frequencies having a center frequency ranging from 0.5 MHz to about 80 MHz, including center frequencies of 4 MHz, 8 MHz, 10 MHz, 12 MHz, 20 MHz, 40 MHz, 60 MHz, and any other suitable frequency, both greater and smaller. The frequency band emitted by the intraluminal imaging device may have a bandwidth, which may be referred to in terms of a percentage of the center frequency. For example, the bandwidth may range from approximately 1% to approximately 200%, including values such as 10%, 25%, 50%, 100%, 150%, and any other suitable bandwidth, both greater and smaller.

The stent struts 230 may be strong linear reflectors at the transmitting frequency of the imaging device 102. Further, in some aspects, the stent struts 230 may exhibit nonlinear reflective properties, such that the echoes produced by the stent struts 230 comprise a different range or collection of frequencies than the frequencies transmitted by the imaging device 102. In some aspects, the stent struts 230 may produce harmonic reflections in addition to linear reflections. It may be desirable, in some instances, to visualize and identify the stent struts 230 using the nonlinear reflections to confirm proper positioning, treatment effectiveness, etc.

Figure 4:
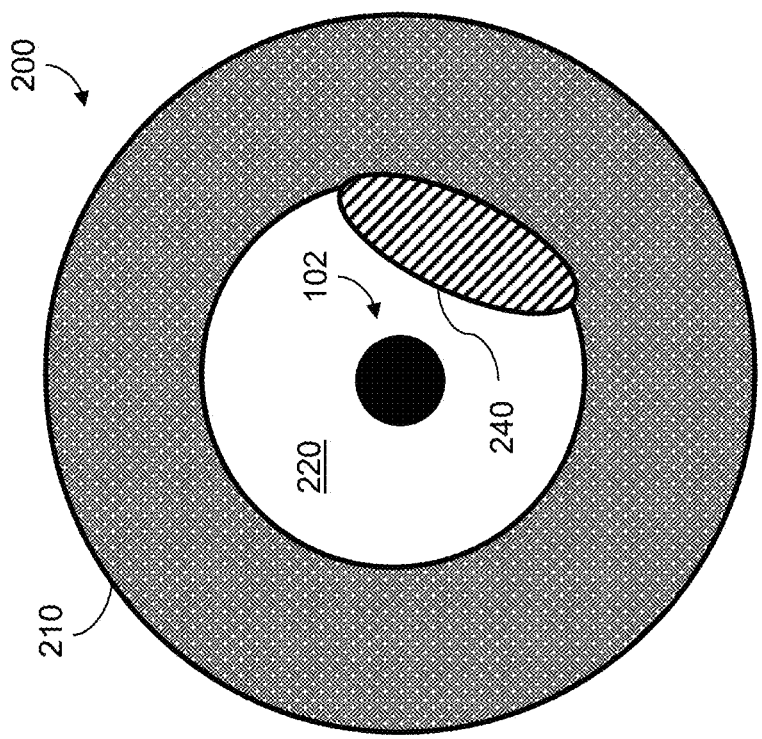
FIG. 4 is a diagrammatic cross-sectional view of a blood vessel including a stenosis, according to aspects of the present disclosure.

FIG. 4 is a diagrammatic cross-sectional view of a blood vessel 200 that includes a calcium deposit 240 on a wall 210 of the vessel 200. As described above with respect to FIG. 3, the wall 210 of the vessel 200 in FIG. 4 may comprise the tissue structure that defines the lumen 220 of the vessel 200. An intraluminal imaging device 102, which may include an IVUS imaging catheter, is positioned within the lumen 220. Similar to the stent struts 230 shown in FIG. 3, the calcium deposit 240 shown in FIG. 4 may exhibit nonlinear reflective properties, such that the echoes produced by the calcium deposit 240 comprise a different range or collection of frequencies than the frequencies transmitted by the imaging device 102. In some aspects, the calcium deposit 240 may produce harmonic reflections in addition to linear reflections. It may be desirable, in some instances, to visualize and identify the calcium deposit 240 to assess the severity of the blockage or restriction of the lumen 220 caused by the calcium deposit 240 or to plan treatment.

Figure 5:
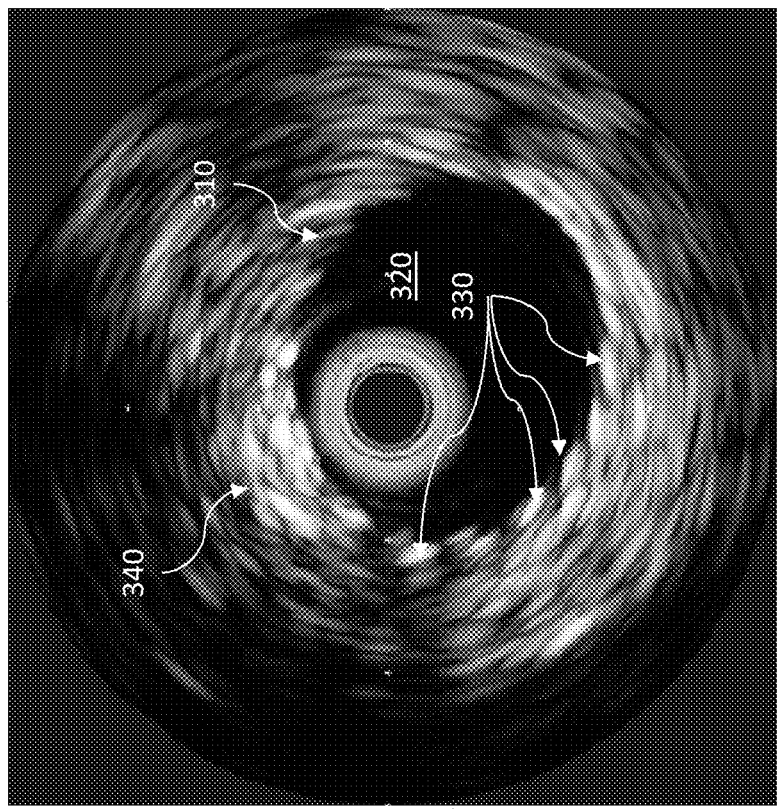
FIG. 5 is an intravascular ultrasound (IVUS) image of a blood vessel, according to aspects of the present disclosure.

In some instances, the stent struts 230 and calcium deposit 240 shown in FIGS. 3 and 4 may not be easily identifiable in conventional ultrasound images, such as B-mode IVUS images. In that regard, FIG. 5 shows a B-mode IVUS image 300 of a vessel that includes stent struts 330 and a calcium deposit 340. The stent struts 330 appear as periodically-arranged bright spots positioned around the lumen 320 of the vessel on an interior surface of the vessel wall 310. The calcium deposit 340 appears as a bright blob or portion in the image outside the lumen 320. As illustrated, it may be challenging to distinguish these different features from one another in the B-mode image 300. For example, the brightness of the vessel wall 310 and other tissue structures may vary in the blood vessel such that the difference in brightness between the vessel wall 310 and the calcium deposit 340 is less noticeable. Accordingly, assessment of these features may be imprecise, and may require significant expertise and experience to identify the features.

Figure 6:
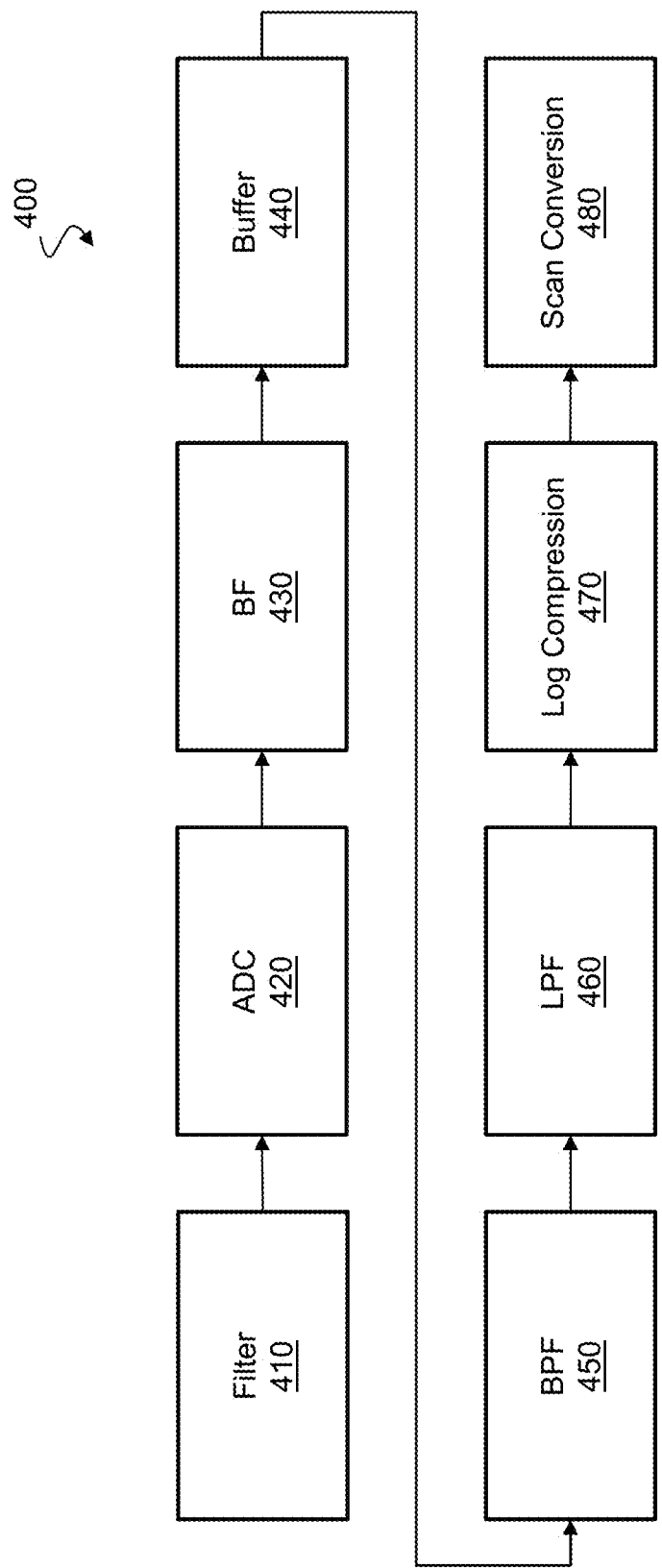
FIG. 6 is a diagrammatic schematic view of a system for visualizing nonlinear reflectors in an ultrasound image, according to aspects of the present disclosure.

FIG. 6 is a schematic diagram of a system 400 for identifying and visualizing nonlinear reflectors in an ultrasound image, according to an embodiment of the present disclosure. It will be understood that the elements of the system 400 may comprise computer program code or instructions executable by a processor circuit, such as the processor circuit 150 shown in FIG. 2. For example, in some embodiments, the elements of the system 400 comprise different processing modules. In some embodiments, the elements of the system 400 comprise different hardware components.

In some embodiments, the components of the system 400 are implemented by the PIM 104 shown in FIG. 1. In some embodiments, the components of the system 400 are implemented by the processing system 106. In some embodiments, the components of the system 400 are distributed between the intraluminal imaging device 102, the PIM 104, and/or the processing system 106. The components of the system 400 can be implemented via a combination of hardware and software components, and may be executed by the processor circuit 150 described above with respect to FIG. 2.

The system of FIG. 6 comprises a filter 410 configured to receive raw analog electrical signals from an ultrasound transducer of an intraluminal ultrasound imaging device, and perform filtering on the signals. The analog ultrasound signals may include backscatter signals generated by the intraluminal ultrasound device at a variety angular position (e.g., at θ, 2×θ, 3×θ, . . . ) around a circumference of the device. The filtering performed by the filter 410 may include, for example, band pass filtering, noise filtering, etc.

The filter 410 may be configured with cutoff frequencies such that noise outside frequencies of interest is reduced in the output signal. The system 400 further includes an analog-to-digital converter (ADC) 420 configured to receive the filtered analog ultrasound signal from the filter 410. The ADC 420 is further configured to sample the analog ultrasound signal to provide digital ultrasound signals or data. The digital ultrasound signals or data may include a plurality of scanlines each including a sequence of real-valued radiofrequency (RF) samples along an imaging depth (e.g., a radial axis of the imaging device) as described in greater detail herein.

The digital ultrasound signals are then passed to a beamformer (BF) 430 configured to perform a coherent delay-and-sum operation on the image signals to provide beamformed signals. In some aspects, the BF 430 may perform a baseband conversion and/or demodulation on the image signals. In some embodiments, the BF 430 may include a rectifier configured to convert the real-valued RF samples in the image signals to baseband (BB) signal signals or data including complex in-phase, quadrature-phase (IQ) pairs. The rectifier may perform down-conversion, low-pass filtering, and/or decimation. The down-conversion converts the RF output signal data from the RF to BB, for example, by down-mixing the RF signals with two sinusoidal signals with a 90 degrees phase difference.

The beamformed data is then passed to a buffer 440, which may include a memory device configured to temporarily store the beamformed image data for further processing. The buffer 440 may comprise a volatile memory resource that is either accessible to a single processing unit (e.g., CPU core or FPGA) or a shared memory accessible to multiple processors (e.g., multiple cores, GPU, and/or multiple paths within an FPGA). In some embodiments, the buffer 440 comprises a duplicator configured to duplicate the image data to be processed along different processing paths. As described further below, the processing paths may be configured to perform operations on the image data simultaneously or at different times. The beamformed data is then received by a band pass filter (BPF) 450, which performs additional filtering on the data. In that regard, the BPF 450 may be configured to perform different filtering operations on the data to provide different filtered data or signals. In some aspects, the BPF 450 may comprise a first band pass filter associated with a first frequency or frequency band, and a second band pass filter associated with a second frequency or frequency band. In particular, the BPF 450 may be configured to apply a first band pass filter to the beamformed image data that will be used to generate a first ultrasound image, and a second band pass filter to the same beamformed image data that will be used to generate a second ultrasound image.

In some aspects, the different band pass filters may comprise, or correspond to, different processing paths in the system than can perform separate operations on the image data, either simultaneously or at different times. In some embodiments, the first band pass filter may correspond to the frequencies transmitted by the ultrasound transducer. Accordingly, in some embodiments, the first ultrasound image may comprise a B-mode image configured to show tissue structures of the imaged vessel. Further, the second band pass filter may correspond to other frequencies representative of nonlinear portions of the beamformed image data. Accordingly, in some embodiments, the second ultrasound image comprises a nonlinear image showing nonlinear reflectors of the imaged vessel.

In some embodiments, the second band pass filter is associated with a higher range of frequencies than the first band pass filter. In some embodiments, the second band pass filter is associated with one or more harmonic frequencies of the frequencies transmitted by the ultrasound transducer and/or of the first band pass filter. For example, in one embodiment, the first band pass filter has a center frequency of 20 MHz, and the second band pass filter has a center frequency of 40 MHz. Accordingly, in some embodiments, the second band pass filter has a center frequency of twice the center frequency of the first band pass filter and/or of the transmitted frequency. In some embodiments, the second band pass filter may be associated with higher-order harmonics of the transmitted frequency. For example, the second band pass filter may comprise a center frequency of 4X, 8X, or any other suitable multiple of the transmitted frequency band. In some embodiments, the first and second band pass filters are overlapping. In some embodiments, the first and second band pass filters do not overlap. In some embodiments, the second band pass filter comprises a band that is narrower than the first band pass filter.

The filtered data is then passed to a low pass filter (LPF) 460 configured to perform low pass filtering on the image data. In particular, the LPF 460 may be configured to remove or reduce side lobes or noise outside a desired frequency bandwidth. The low-pass-filtered data is then passed to a log compression module 470 that performs log compression. In particular, the log compression module 470 may be configured to reduce the dynamic range of the image data for efficient display. For example, the dynamic range of the image data may be mapped to a logarithmic curve. In some examples, the log compression module 470 may perform the mapping based on a table lookup, where the table may be encoded with a log compression curve. In some embodiments, the image data undergoes an envelope detection operation before or after the log compression.

A scan conversion module 480 is coupled to the log compression module 470 and configured to perform scan conversion on the image data output by the log compression module 470 to a suitable display format. In an example, the image data may be in a polar coordinate and the scan conversion module 480 may convert the image data into Cartesian coordinates for display.

Figure 7:
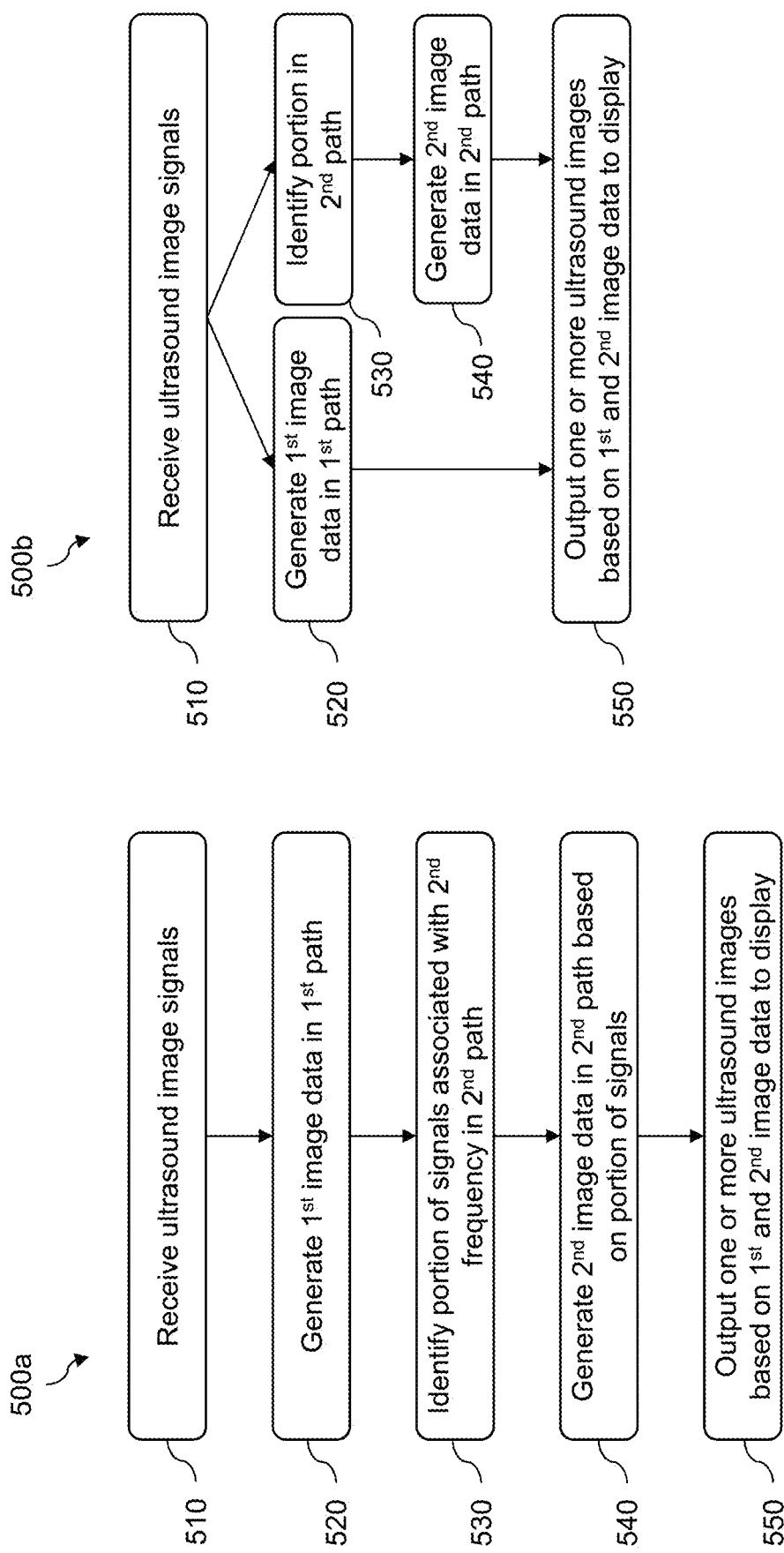
FIG. 7a is a flow diagram of a method for visualizing nonlinear reflectors in an ultrasound image using a single processing thread, according to aspects of the present disclosure.
FIG. 7b is a flow diagram of a method for visualizing nonlinear reflectors in an ultrasound image using different parallel processing threads, according to aspects of the present disclosure.

FIGS. 7a and 7b are flow diagrams illustrating respective methods 500a, 500b for visualizing reflectors in an ultrasound image, according to aspects of the present disclosure. In that regard, FIG. 7a illustrates a method 500a for visualizing reflectors using a single processing thread in which first and second processing paths occur at different times. For example, the method 500a may be performed using a buffer 440 and/or duplicator as described above with respect to FIG. 6. FIG. 7b illustrates a method 500b in which first and second processing paths occur simultaneously using different processing threads. Referring to FIGS. 500a and 500b, it will be understood that one or both of the methods 500a, 500b may be performed using one or more of the systems and devices described above, including the intraluminal ultrasound imaging system 100, the processor circuit 150, and/or the system 400. In step 510, a processor circuit receives ultrasound image signals from an intraluminal ultrasound imaging device, such as an IVUS catheter. The ultrasound image signals are electrical signals. In some embodiments, the ultrasound image signals are digital signals. In other embodiments, the image signals are analog signals, such as raw signals provided by the acoustic elements of the transducer array. In some embodiments, the ultrasound image signals comprise image data. The image signals may be representative of a blood vessel that includes a nonlinear reflector, such as a stent and/or a calcium deposit. The ultrasound image signals are obtained by the intraluminal ultrasound imaging device by emitting ultrasound pulses at a transmit frequency or band. For example, the transmit frequency band may comprise a center frequency of 2 MHz, 5 MHz, 10 MHz, 20 MHz, 40 MHz, 60 MHz, or any other suitable frequency, both greater and smaller. The transmit frequency band may also comprise a bandwidth, which may be described as a percentage of the center frequency (e.g., 50%, 100%, 150%, etc.).

Figure 8:
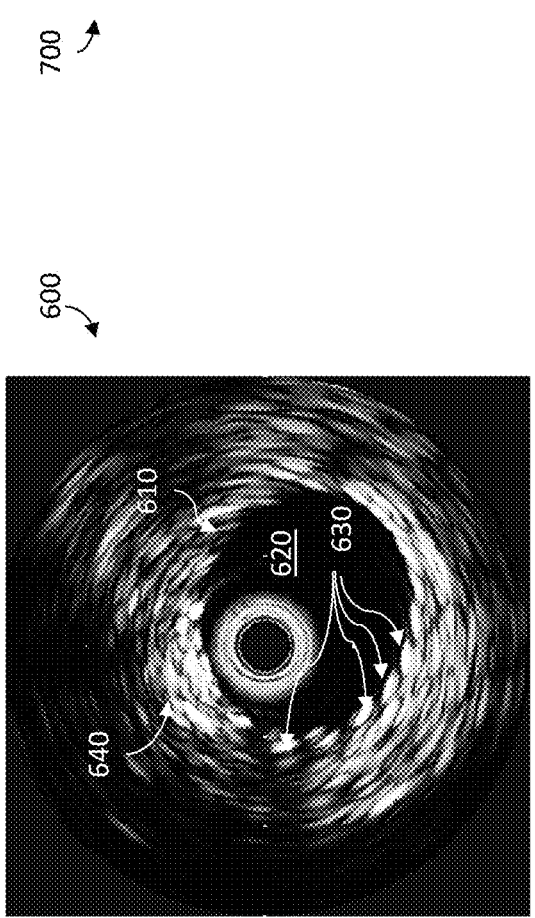
FIG. 8 is an IVUS image of a blood vessel, according to aspects of the present disclosure.

In step 520, the processor circuit generates, in a first processing path, first ultrasound image data based on the ultrasound image signals. As described above, in some embodiments, the first processing path and the second processing path occur simultaneously and in parallel on different processing threads, as in FIG. 7b. Processing schemes and systems for parallel multipath processing are described in, for example, U.S. Patent Application Publication 2014/0180105, the entirety of which is incorporated by reference. In other embodiments, the first and second processing paths are performed on a same thread at different times, as in FIG. 7a. This may be possible using a buffer or memory device (e.g., buffer 440 in FIG. 6) configured to temporarily store and create two or more copies of the image signals and/or image data such that the copies of the image data can be processed on two or more parallel paths. Generating the first ultrasound image data may comprise applying a first band pass filter to the image signals. The first band pass filter may be associated with the transmit frequency such that the first bandpass filter is configured to remove noise and image artifacts from the image signals. In some embodiments, the first ultrasound image data generated in step 520 comprises B-mode image data representative of both linear and nonlinear reflectors. In some embodiments, the B-mode image data is representative of only linear reflectors. In that regard, FIG. 8 shows a B-mode IVUS image 600 based on the first or linear ultrasound image data generated in step 520. The B-mode image 600 includes anatomical features, such as a vessel wall 610, a lumen 620, and a calcium deposit (e.g., plaque) 640. The B-mode image 600 also includes a plurality of stent struts 630. As described above, all of the features shown in the B-mode image 600 reflect linear ultrasound signals, which comprise the frequencies emitted by the ultrasound transducer array. However, as described below, some of the features, including the stent struts 630 and the calcium deposits 640, may also generate and/or reflect substantial amounts of nonlinear ultrasound signals.

In step 530, the processor circuit identifies, in a second processing path, a portion of the image signals associated with nonlinear reflections. The nonlinear portion of the image signals is associated with a second frequency that is different from the transmit frequency. Identifying the nonlinear portion of the image signals may comprise applying a second band pass filter to the image signals that is different from the first band pass filter applied in step 520. For example, the second band pass filter may be associated with nonlinear frequencies (e.g., harmonics) of the transmit frequency. In some aspects, the second band pass filter may remove or reduce portions of the image signals associated with linear reflectors, such as tissue. In some embodiments, the second frequency and the transmit frequency may cover different, non-overlapping ranges. In some embodiments, the ranges of the second frequency and the transmit frequency overlap. In some embodiments, the second frequency comprises a subset of frequencies of the transmit frequency and/or of the first frequency.

In step 540, the processor circuit generates, in the second processing path, second ultrasound image data based on the identified nonlinear portion of the image signals. In some aspects, the second ultrasound image data may be referred to as nonlinear image data. Accordingly, the second or nonlinear image data generated in step 540 may show nonlinear reflectors having a greater relative intensity than linear reflectors, for example. In some embodiments, the nonlinear image data is representative of only nonlinear reflectors.

Figure 9:
FIG. 9 is an IVUS image of nonlinear reflectors in a blood vessel, according to aspects of the present disclosure.

FIG. 9 is a nonlinear image 700 based on the nonlinear image data generated in step 540, according to some embodiments of the present disclosure. In that regard, the nonlinear image 700 shows a plurality of nonlinear reflectors, including stent struts 730 and calcium deposits 740. It will be understood that the nonlinear image 700 shows fewer features and has a lower overall intensity than the linear B-mode image 600 shown in FIG. 8. In some aspects, because the nonlinear image 700 is generated using nonlinear portions of the image data, some vessel features which are linear reflectors, such as a vessel wall, do not appear in the nonlinear image 700. In some aspects, the nonlinear image 700 may be associated with frequencies higher than those of the standard B-mode image 600 shown in FIG. 8. For example, the nonlinear image 700 may be associated with harmonic frequencies of the frequencies used to generate the linear B-mode image 600. Accordingly, the nonlinear image 700 shown in FIG. 9 may exhibit increased lateral resolution and/or axial resolution when compared to the B-mode image 600 of FIG. 8. For example, the B-mode image 600 and the nonlinear image 700 both show stent struts 630, 730. However, the nonlinear image 700 shows the stent struts 730 with an increased lateral resolution and/or axial resolution. Accordingly, the stent struts 730 appear smaller and are more defined in the nonlinear image 700 of FIG. 9 than in the B-mode image 600 of FIG. 8.

In step 550, the processor circuit outputs one or more ultrasound images generated based on the first and second ultrasound image data to a display in communication with the processor circuit. In some embodiments, the processor circuit is configured to generate and output a first ultrasound image based on the first image data and a second ultrasound image based on the second image data. In some embodiments, the processor circuit is configured to display the first and second ultrasound images separately, or side-by-side. In some embodiments, the one or more images may comprise a first ultrasound image generated based on the linear ultrasound image data and a graphical representation of the nonlinear image. For example, the graphical representation of the nonlinear image may comprise all or a portion of the nonlinear image. In some embodiments, the graphical representation comprises one or more indicators showing the locations of one or more nonlinear reflectors within a field of view, which can be displayed over the first ultrasound image (e.g., linear B-mode image). In some embodiments, outputting the ultrasound images includes generating a composite image based on the ultrasound image and the nonlinear image. Generating the composite image may include overlaying the nonlinear image, or one or more portions of the nonlinear image, on the ultrasound image such that the composite image indicates a location of one or more nonlinear reflectors in the ultrasound image. In some embodiments, the overlaid portions of the nonlinear image comprise a different representation than the ultrasound image. For example, the graphical representation of the nonlinear image may be of a different color than the ultrasound image.

Figure 10:
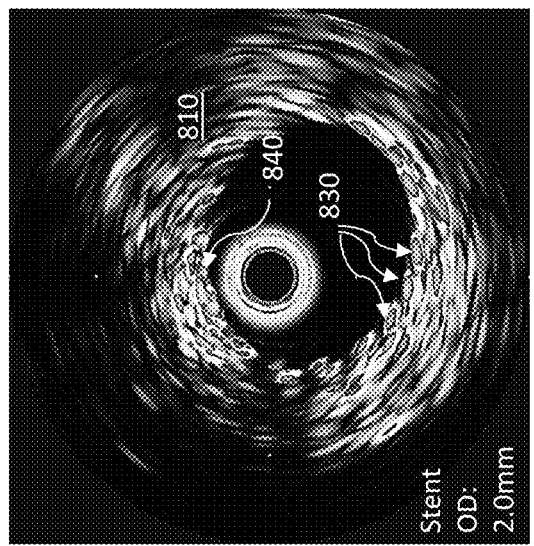
FIG. 10 is a composite image including the nonlinear reflectors shown in the IVUS image of FIG. 9 overlaid on the IVUS image of FIG. 8, according to aspects of the present disclosure.

FIG. 10 shows a composite image 800 that includes graphical representations 830, 840 overlaid on a B-mode image 810, where the graphical representations 830, 840 are representative of nonlinear image data. In the composite image 800, the graphical representations may include an overlay of all or a substantial portion of the nonlinear image 700 shown in FIG. 9 on the linear B-mode image 600 shown in FIG. 8. The graphical representations 830, 840 include all or portions of the nonlinear image 700, and are modified or represented to distinguish between the linear portions of the B-mode image 810. For example, the nonlinear image portions 830, 840 may be colored differently from the B-mode image 810, may be shown with a different brightness, contrast, or with other markers, including outlines or a patterned appearance. The composite image 800 further includes a graphical representation that is a numerical representation associated with the second ultrasound image 700. In particular, the graphical representation 850 is a numerical representation of a geometric measurement of the stent shown in FIG. 9. More specifically, the graphical representation 850 is a numerical representation of the diameter of the stent shown in FIG. 9. However, the graphical representation 850 may include other numerical representations, such as lumen size, stenosis size, vessel wall outside diameter, etc. In some embodiments, step 550 includes performing one or more image processing operations on the nonlinear image before generating the graphical representation. For example, in some embodiments, spatial filtering is applied to the nonlinear image 700 to reduce noise and/or speckle. In some embodiments, one or more of an erosion, dilation, or segmentation operation is performed to identify or distinguish contiguous groups of pixels corresponding to nonlinear reflectors, such as stent struts and calcium deposits.

In some aspects, axial and/or lateral resolution may be substantially improved using the nonlinear imaging techniques described above for a variety of back-end gain values. By showing nonlinear portions in an image overlaid on linear portions of the image, physicians may have increased confidence of the position of nonlinear reflectors (e.g., stent struts), and in the identification of calcium deposits and other naturally-occurring conditions within a lumen. Further, back-end gain can be adjusted, either automatically by the processor circuit or by a user via a user input device, to further improve the resolution of nonlinear images. In some embodiments, a back-end gain is automatically set or configured for the nonlinear image, which may be different from the back-end gain applied for the linear or B-mode image. Additionally, other imaging and/or image processing parameters may be adjusted to effect further improvements in resolution, reduction in noise, reduction in artifacts, etc. For example, the pulse repetition frequency (PRF), pulse length, and any other suitable imaging parameter may be adjusted to improve and/or optimize image characteristics of the linear and/or nonlinear images.

In some embodiments, the processor circuit is configured to output the ultrasound image and the nonlinear image beside the ultrasound image. In some embodiments, the graphical representation generated by the processor circuit includes a numerical representation associated with the nonlinear ultrasound image. In some embodiments, the numerical representation represents a geometric value of a nonlinear reflector computed by the processor circuit. For example, in some embodiments, the geometric value may comprise a size (e.g., diameter) of a stent, a size (e.g., cross-sectional area) of a calcium deposit, or any other suitable geometric value associated with the nonlinear reflector. In some embodiments, the processor circuit is configured to control the intraluminal ultrasound imaging device to obtain flow data, such as doppler ultrasound data, and to generate one or more doppler images representative of blood flowing through the lumen. In some embodiments, the processor circuit is further configured to include a graphical representation of the doppler data onto the B-mode image with the graphical representation of the nonlinear image.

Examples of different image processing, image analysis, border detection, and/or pattern recognition algorithms include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors, U.S. Pat. No. 7,463,759 entitled "SYSTEM AND METHOD FOR VASCULAR BORDER DETECTION" issued Dec. 9, 2008 with Jon D. Klingensmith, Anuj a Nair, Barry D. Kuban and D. Geoffrey Vince, as inventors, U.S. Pat. No. 9,265,481 entitled "SYSTEM AND METHOD FOR EQUALIZING RECEIVED INTRAVASCULAR ULTRASOUND ECHO SIGNALS" issued Feb. 23, 2016 with Andrew Hancock and Dale Gene Dorando as inventors, U.S. Pat. No. 10,269,096 entitled "CLUTTER SUPPRESSION FOR SYNTHETIC APERATURE ULTRASOUND" issued Apr. 23, 2019 with Andrew Hancock as the inventor, and U.S. Pat. Pub. No. 2014/0100440 entitled "SYSTEM AND METHOD FOR INSTANT AND AUTOMATIC BORDER DETECTION" published Apr. 10, 2014 with AJ Cheline, Fergus Merritt, Asher Cohen, Elizabeth Begin, Nathaniel J. Kemp, Jason Sproul, and Badr Elmaanaoui, as inventors, the teachings of which are hereby incorporated by reference herein in their entirety. Other algorithms, whether related to these or not, may be employed instead or in addition.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. For example, while embodiments described above refer specifically to IVUS imaging catheters, it will be understood that other imaging modalities and imaging devices can be used without departing from the scope of the present disclosure, including forward looking intravascular ultrasound (FL-IVUS) imaging, intravascular photoacoustic (IVPA) imaging, intracardiac echocardiography (ICE), transesophageal echocardiography (TEE), optical coherence tomography (OCT), and/or other suitable imaging modalities. It is understood that such variations may be made to the foregoing without departing from the scope of the present disclosure. Accordingly, it is appropriate that the appended claims be construed broadly and in a manner consistent with the present disclosure.

What is claimed is:

1. An apparatus for visualizing a reflector in a blood vessel of a patient, comprising:
   an intravascular ultrasound (IVUS) imaging catheter comprising a transducer array; and
   a processor circuit communicatively coupled to the IVUS imaging catheter, wherein the processor circuit is configured to:
   receive, from the IVUS imaging catheter, IVUS image signals, wherein a first portion of the IVUS image signals are representative of first echoes produced by a plurality of linear reflectors and second portion of the IVUS image signals are representative of second echoes produced by one or more nonlinear reflectors such that the first portion of the IVUS image signals and the second portion of the IVUS image signals are obtained by the transducer array while positioned at a location along a length of the blood vessel,
   wherein the first echoes produced by the plurality of linear reflectors comprise a first frequency matching a transmit frequency of the IVUS imaging catheter, and
   wherein the second echoes produced by the one or more nonlinear reflectors comprise a second frequency different than the transmit frequency of the IVUS imaging catheter,
   generate a first IVUS image based on the first portion of the IVUS image signals;
   generate a different, second IVUS image based on the second portion of the IVUS image signals; and
   output, to a display in communication with the processor circuit, the first IVUS image and the second IVUS image such that the first IVUS image and the second IVUS image are displayed simultaneously and proximate to one another, wherein the first IVUS image and the second IVUS image show the blood vessel at the location where the transducer array was positioned.

2. The apparatus of claim 1, wherein the processor circuit is configured to:
   apply a first bandpass filter to the first portion of the IVUS image signals to generate the first IVUS image; and
   apply a second bandpass filter to the second portion of the IVUS image signals to generate the second IVUS image;
   wherein the first bandpass filter is associated with a first frequency band that includes the transmit frequency, and wherein the second bandpass filter is associated with a second frequency band that includes a harmonic of the transmit frequency and is non-overlapping with the first frequency band.

3. The apparatus of claim 2, wherein the second frequency band is higher than the first frequency band.

4. The apparatus of claim 1, wherein the processor circuit is configured to output, to the display, a numerical representation associated with the second IVUS image.

5. The apparatus of claim 4, wherein the processor circuit is configured to compute a geometrical value of the nonlinear reflector based on the second portion of the IVUS image signals, and wherein the numerical representation represents the geometrical value.

6. The apparatus of claim 1, wherein the processor circuit is configured to generate a composite image based on the first IVUS image and the second IVUS image.

7. The apparatus of claim 6, wherein the processor circuit is configured to generate the composite image by overlaying the second IVUS image on the first IVUS image, and
wherein portions of the composite image corresponding to the second IVUS image comprise a different color from portions of the composite image corresponding to the first IVUS image.

8. The apparatus of claim 1,
wherein the first IVUS image is generated by a first processing thread, and
wherein the second IVUS image is generated by a second processing thread.

9. A method for visualizing a reflector in a blood vessel of a patient, comprising:
receiving intravascular ultrasound (IVUS) image signals obtained by an IVUS imaging catheter comprising a transducer array, wherein a first portion of the IVUS image signals are representative of first echoes produced by a plurality of linear reflectors and a second portion of the IVUS image signals are representative of second echoes produced by a one or more nonlinear reflectors such that the first portion of the IVUS image signals and the second portion of the IVUS image signals are obtained by the transducer array while positioned at a location along a length of the blood vessel, wherein the first echoes produced by the plurality of linear reflectors comprise a first frequency matching a transmit frequency of the IVUS imaging catheter, and wherein the second echoes produced by the one or more nonlinear reflectors comprise a second frequency different than the transmit frequency of the IVUS imaging catheter;
generating a first IVUS image based on the first portion of the IVUS image signals;
generating a different, second IVUS image based on the second portion of the IVUS image signals; and
outputting, to a display, the first IVUS image and the second IVUS image such that the first IVUS image and the second IVUS image are displayed simultaneously and proximate to one another, wherein the first IVUS image and the second IVUS image show the blood vessel at the location where the transducer array was positioned.

10. The method of claim 9, further comprising:
applying a first bandpass filter to the first portion of the IVUS image signals to generate the first IVUS image; and
applying a second bandpass filter to the second portion of the IVUS image signals to generate the second IVUS image,
wherein the first bandpass filter is associated with a first frequency band that includes the transmit frequency, and wherein the second bandpass filter is associated with a second frequency band that includes a harmonic of the transmit frequency and is non-overlapping with the first frequency band.

11. The method of claim 10, wherein the second frequency band is higher than the first frequency band.

12. The method of claim 9, further comprising:
generating a numerical representation associated with the second IVUS image; and
outputting the numerical representation to the display.

13. The method of claim 12, wherein generating the numerical representation comprises computing a geometrical value of the nonlinear reflector.

14. The method of claim 9, wherein outputting to the display further comprises generating a composite image based on the first IVUS image and the second IVUS image.

15. The method of claim 14, wherein generating the composite image comprises overlaying the second IVUS image on the first IVUS image, and
wherein portions of the composite image corresponding to the second IVUS image comprise a different color from portions of the composite image corresponding to the first IVUS image.

* * * * *